United States Patent
Odom et al.

(10) Patent No.: US 10,954,201 B2
(45) Date of Patent: Mar. 23, 2021

(54) TWO-ELECTRON DONATING PHENOTHIAZINES AND USE THEREOF

(71) Applicant: University of Kentucky Research Foundation, Lexington, KY (US)

(72) Inventors: Susan A. Odom, Lexington, KY (US); Aman Preet Kaur, Lexington, KY (US); Matthew D. Casselman, Lexington, KY (US); N. Harsha Attanayake, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 15/683,679

(22) Filed: Aug. 22, 2017

(65) Prior Publication Data
US 2018/0057471 A1 Mar. 1, 2018

Related U.S. Application Data

(60) Provisional application No. 62/378,443, filed on Aug. 23, 2016.

(51) Int. Cl.
| | |
|---|---|
| *H01M 8/18* | (2006.01) |
| *C07D 279/28* | (2006.01) |
| *H01M 8/1018* | (2016.01) |
| *C08G 65/00* | (2006.01) |
| *C08G 65/334* | (2006.01) |

(52) U.S. Cl.
CPC ......... *C07D 279/28* (2013.01); *C08G 65/002* (2013.01); *C08G 65/3348* (2013.01);
(Continued)

(58) Field of Classification Search
CPC .. C07D 279/28; C08G 65/00; C08G 65/3348; C08G 65/002; H01M 8/186; H01M 8/1018; H01M 8/18; H01M 8/188
See application file for complete search history.

(56) References Cited

U.S. PATENT DOCUMENTS 4,439,280 A * 3/1984 Gendler ............... C09B 21/00
  205/55
5,565,402 A * 10/1996 Tsuchida ............... B41M 5/323
  503/216
(Continued)

FOREIGN PATENT DOCUMENTS

JP   H03114878   *  5/1991
JP   10006687    *  1/1998
(Continued)

OTHER PUBLICATIONS

Lucarini et al. J. Am. Chem. Soc. 1999, 121, 11546-11553 (Year: 1999).*
(Continued)

*Primary Examiner* — Alexander Usyatinsky
(74) *Attorney, Agent, or Firm* — Stites & Harbison PLLC; Mandy Wilson Decker

(57) ABSTRACT

Compounds for use as electrolyte in a non-aqueous redox battery are provided, including an N-substituted phenothiazine compound according to the formula:

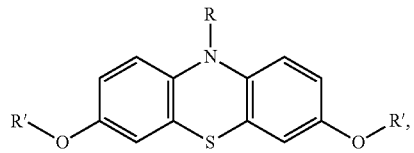

R' is alkyl and R is selected from alkyl, aryl, alkylaryl, alkoxyaryl, alkylcarboxyl, arylcarbonyl, haloalkyl, perfluoroalkyl, glycol, polyether, haloaryl, a negative electrolyte, a polymerizable unit, and a polymer.

2 Claims, 5 Drawing Sheets

(52) U.S. Cl.
CPC .......... *H01M 8/1018* (2013.01); *H01M 8/18* (2013.01); *H01M 8/186* (2013.01); *H01M 8/188* (2013.01); *C08G 2650/62* (2013.01); *C08G 2650/64* (2013.01)

(56) References Cited

U.S. PATENT DOCUMENTS 5,811,548 A * 9/1998 Bannwarth .......... C07D 279/22 544/101
2017/0062842 A1    3/2017 Huang et al.

FOREIGN PATENT DOCUMENTS

| JP | 2005128289 | * | 5/2005 |
| WO | WO 99/45081 | * | 3/1999 |
| WO | WO 99/45081 | * | 9/1999 |

OTHER PUBLICATIONS

Cadogan et all. J. Chem. Soc. (C) 1970, 2437-2441 (Year: 1970).*
Ergun et all. Chem. Commun., 2014, 50, 5339-5341 (Year: 2014).*
JPH03114878MT (Year: 1991).*
J. Am. Chem. Soc. 1999, 121, 11546-11553 (Year: 1999).*
Pereţeanu et al. Org. Biomol. Chem., 2013, 11, 5127-5135. (Year: 2013).*
JP2005128289 MT (Year: 2005).*
Muruyama et. al.al. Niigata Igakkai Zasshi (1968), 82(9), 595-606 Maruyama (Abstract)). (Year: 1968).*
CN 104478870 (Abstract) (Year: 2015).*
Jackson, et al. Journal of Medicinal Chemistry (1968), 11(3), 622-3 (Abstract) (Year: 1968).*
Journal of the American Chemical Society (1999), 121(49), 11546-11553. (Abstract) (Year: 1999).*
Huang, et al., A Two-Electron Storage Nonaqueous Organic Redox Flow Battery, Adv. Sustainable Syst. 2018, 2, 1700131, 1-6.

* cited by examiner

TWO-ELECTRON DONATING PHENOTHIAZINES AND USE THEREOF

PRIORITY

This invention claims priority to U.S. Provisional Application Ser. No. 62/378,443, filed Aug. 23, 2016.

GOVERNMENT INTEREST

This invention was made with government support under grant numbers 1300653 and 1355438 awarded by the National Science Foundation. The government has certain rights in the invention.

TECHNICAL FIELD

The presently-disclosed subject matter generally relates to phenothiazine derivatives. In particular, certain embodiments of the presently-disclosed subject matter relate to phenothiazine derivatives having stable first and second oxidation states and the use thereof for redox flow batteries.

INTRODUCTION

Redox flow batteries (RFBs), which function by storing electrochemical energy in liquid electrolyte formulations, are promising technologies for energy storage on medium to large scales.[1] Since the energy is stored in a liquid form, increasing the capacity of RFBs is largely a matter of increasing the size of active-material storage tanks. Current state-of-the-art RFBs are based upon aqueous vanadium chemistry. While such RFBs are robust and long-lived, they rely upon expensive transition metals as active materials that form redox active species. Additionally, these RFBs are aqueous-based and, therefore, are limited by the electrochemical stability window of water (about 1.5 V).[2]

One possibility for accessing higher voltages includes the use of non-aqueous electrolytes, which are generally not compatible with transition metal-based active materials. Although such systems have the potential for increasing the voltage of the system and reducing cost by exchanging scarce transition metals for plentiful carbon-based materials, the development and commercialization of organic non-aqueous redox flow batteries is largely in its infancy due to challenges in long term stability,[3] atom economy,[4] and solubility/energy density.[5]

For example, due to stability requirements for extended periods of time in both neutral and oxidized forms, only a limited number of molecular classes have been used for catholyte (positive electrolyte) material in preliminary all-organic non-aqueous RFBs, including dialkoxybenzenes[6], stabile N-oxo radicals[7], and phenothiaizines.[8,9] These molecules are electron rich and are therefore capable of donating an electron when paired with an anolyte (negative electrolyte) material. However, molecules used as charge storage materials must also function with excellent atom economy. Vanadium-based aqueous RFBs have excellent atom economy with the ability to store an electron with 50 amu of mass. Organic materials, on the other hand, generally have molecular weights of about 150-300 amu due to need for stabilizing structures to allow for reversible electrochemical performance. This presents a challenge for organic non-aqueous systems as this represents a 65-85% reduction in atom economy relative to vanadium. Related to the increased molecular weights of organic materials are the lower concentrations of active species achieved in non-aqueous electrolytes. Only a handful of organic electroactive materials are capable of dissolving at concentrations greater than 0.5M.[7,9]

Accordingly, there exists a need for stable electroactive materials having sufficient atom economy for use in non-aqueous redox flow batteries.

SUMMARY OF INVENTION

The presently-disclosed subject matter includes compounds that can be used stable two-electron redox-active materials. The presently-disclosed subject matter further includes rechargeable batteries, including non-aqueous redox flow batteries and the use of two-electron redox-active materials as electrolytic materials.

In some embodiments of the presently-disclosed subject matter, a compound is provided, with a structure as set forth below

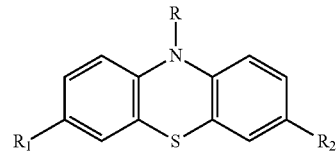

In some embodiments, $R_1$ and $R_2$ are independently selected from H, $N(R')_2$, $N(R'')_2$, OR', OR'', and R'' so long as when $R_1$ is H, $R_2$ is not H. In some instances, R, R' and R'' are independently selected from alkyl, aryl, alkylaryl, alkoxyaryl, alkylcarboxyl, arylcarbonyl, haloalkyl, perfluoroalkyl, glycol, polyether, haloaryl, a negative electrolyte, a polymerizable unit, and a polymer.

In some embodiments, the compound is an N-substituted phenothiazine with a structure represented by:

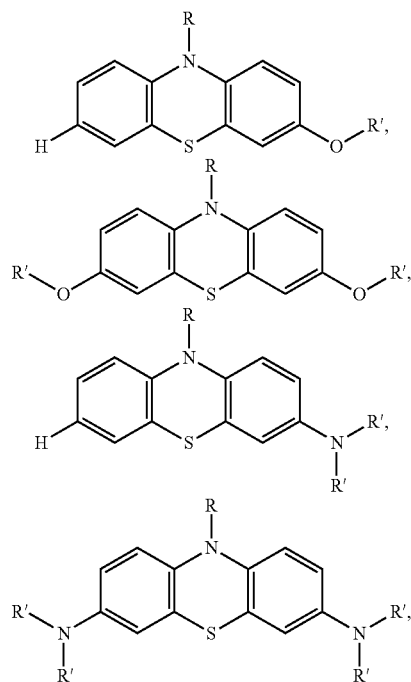

-continued

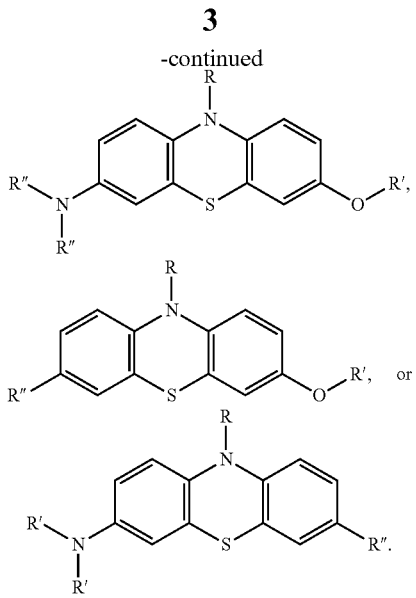

In some embodiments, the N-substituted phenothiazine compounds presently disclosed include one or more solubilizing groups tethered to the phenothiazine core via a linkage at the N-position, also denoted as the 10 position. The solubilizing group tethered to the phenothiazine core can, in some instances, increase solubility of the compound in organic electrolytes. \

In some embodiments, the N-substituted phenothiazine compounds contain one or more electron-donating functional groups attached at the 3 and/or 7 position. Suitable electron-donating functional groups include, but are not limited to, alkoxy groups, amino groups, or a combination thereof. In some embodiments, substituents can be positioned at the 1, 2, 4, 6, 8, and/or 9 positions as long as there is an alkoxy group and/or amino group and/or other suitable electron-donating functional group at the 3 and/or 7 positions. Specifically, the minimum number of substituents the present inventors have demonstrated that is needed is at the 3, 7, and 10 (or 3, 7, and N; N is the same as 10). It is contemplated that the 3 and 10 (N) positions can enable the second charge to be stabilized.

In some embodiments, compounds disclosed herein find use in non-aqueous redox flow batteries. In some instances, the non-aqueous redox flow battery includes a negative electrode immersed in a first non-aqueous liquid electrolyte solution; a positive electrode immersed in a second non-aqueous liquid electrolyte solution, with the second non-aqueous liquid electrolyte solution including a compound as disclosed herein; and a semi-permeable separator interposed between the negative and positive electrodes.

DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

Figure 1:
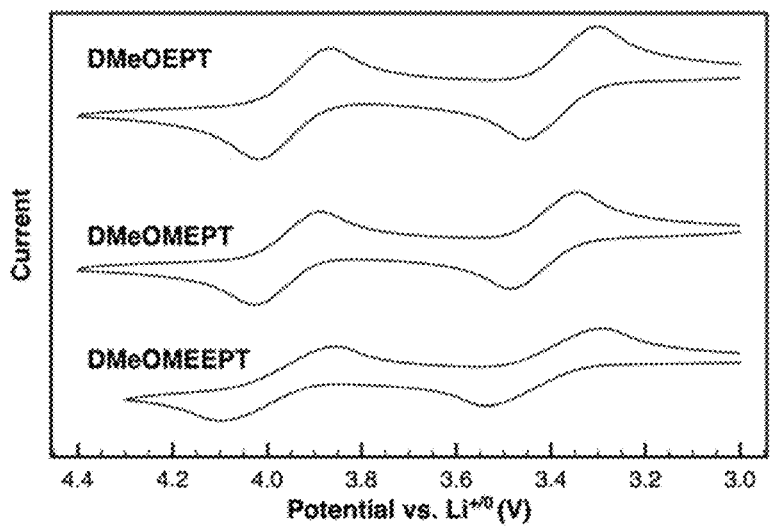
FIG. 1 is a graph showing cyclic voltammograms of DMeOEPT, DMeOMEPT, and DMeOMEEPT, performed with 10 mM analyte in 0.5M $LiPF_6$ in PC at a scan rate of 100 mV/s.

DESCRIPTION OF EXEMPLARY
EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes N-substituted phenothiazine compounds. The phenothiazine forms a redox-active core of the N-substituted phenothiazine compounds. In some embodiments, one or more solubilizing groups may be tethered to the phenothiazine core via a linkage at the N-position. The solubilizing group tethered to the phenothiazine core increases solubility of the compound in organic electrolytes. Additionally or alternatively, in some embodiments, the N-substituted phenothiazine compounds contain one or more electron-donating functional groups attached at the 3 and/or 7 position. Suitable electron-donating functional groups include, but are not limited to, alkoxy groups, amino groups, or a combination thereof.

For example, in some embodiments, the N-substituted phenothiazine compound includes an alkoxyphenothiazine according to the formula set forth below:

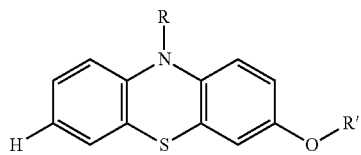

wherein R is an alkyl or (poly)ether and R' is an alkyl.

In some embodiments, the N-substituted phenothiazine compound includes a dialkoxyphenothiazine according to the formula set forth below:

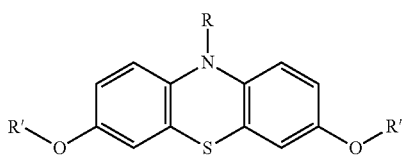

wherein R is selected from alkyl, aryl, alkylaryl, alkoxyaryl, alkylcarboxyl, arylcarbonyl, haloalkyl, perfluoroalkyl, glycol, polyether, haloaryl, a negative electrolyte, a polymerizable unit, and a polymer, and R' is selected from alkyl, aryl, alkylaryl, alkoxyaryl, alkylcarboxyl, arylcarbonyl, haloalkyl, perfluoroalkyl, glycol, polyether, haloaryl, a negative electrolyte, a polymerizable unit, and a polymer.

In some embodiments, the N-substituted phenothiazine compound includes a monoaminophenothiazine according to the formula set forth below:

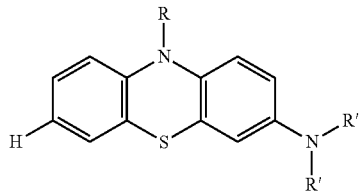

wherein R is selected from alkyl, aryl, alkylaryl, alkoxyaryl, alkylcarboxyl, arylcarbonyl, haloalkyl, perfluoroalkyl, glycol, polyether, haloaryl, a negative electrolyte, a polymerizable unit, and a polymer, and R' is selected from alkyl, aryl, alkylaryl, alkoxyaryl, alkylcarboxyl, arylcarbonyl, haloalkyl, perfluoroalkyl, glycol, polyether, haloaryl, a negative electrolyte, a polymerizable unit, and a polymer.

In some embodiments, the N-substituted phenothiazine compound includes a diaminophenothiazine according to the formula set forth below:

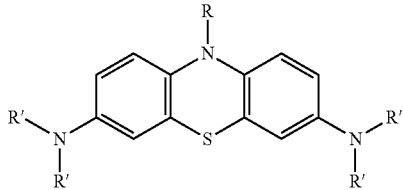

wherein R is selected from alkyl, aryl, alkylaryl, alkoxyaryl, alkylcarboxyl, arylcarbonyl, haloalkyl, perfluoroalkyl, glycol, polyether, haloaryl, a negative electrolyte, a polymerizable unit, and a polymer, and R' is selected from alkyl, aryl, alkylaryl, alkoxyaryl, alkylcarboxyl, arylcarbonyl, haloalkyl, perfluoroalkyl, glycol, polyether, haloaryl, a negative electrolyte, a polymerizable unit, and a polymer.

In some embodiments, the N-substituted phenothiazine compound is according to any one of the following formulae:

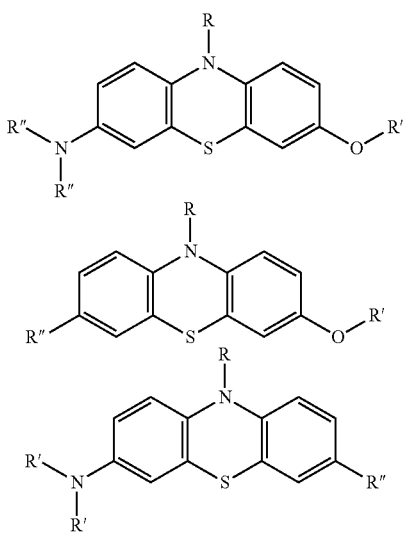

wherein R, R', and R" are independently selected from alkyl, aryl, alkylaryl, alkoxyaryl, alkylcarboxyl, arylcarbonyl, haloalkyl, perfluoroalkyl, glycol, polyether, haloaryl, a negative electrolyte, a polymerizable unit, and a polymer.

Furthermore, in some embodiments of the compound, substituents can be positioned at the 1, 2, 4, 6, 8, and/or 9 positions as long as there is an alkoxy group and/or amino group at the 3 and/or 7 positions. Specifically, the minimum number of substituents the present inventors have demonstrated that is needed is at the 3, 7, and 10 (or 3, 7, and N; N is the same as 10). It is contemplated that the 3 and 10 (N) positions can enable the second charge to be stabilized.

"Alkyl" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Preferably, an alkyl group comprises from 1 to 20 carbon atoms, more preferably, from 1 to 10 carbon atoms.

"Aryl" refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 6 to 20 carbon atoms, more preferably, between 6 to 12 carbon atoms.

"Alkylaryl" refers to an acyclic alkyl in which one of the hydrogen atoms bonded to a carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is ($C_6$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$), more preferably, an arylalkyl group is ($C_6$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Alkoxyaryl" refers to an —O-arylalkyl where arylalkyl is as defined herein.

"Alkylcarboxyl" means a —C(O)R group where R is alkyl, as defined herein.

"Arylcarbonyl" refers to a —C(O)-aryl where aryl is as defined herein.

"Halogen" or "halo" refers to fluorine, chlorine, bromine and iodine. Thus, a haloalkyl, refers to an alkyl group substituted with one or more halogens. A halo aryl refers to an aryl group substituted with one or more halogens.

"Perfluoroalkyl" refers to alkyl groups in which essentially all of the carbon-bonded hydrogen has been replaced by fluorine.

"Polyether" refers to a functional group containing more than one ether, which can include aromatic polyethers such as polyphenyl ether.

Glycols include alcohols in which at least two hydroxyl groups are attached to different carbon atoms in an organic compound, including alkylene glycols such as ethylene glycol and propylene glycol.

A negative electrolyte can include, for example, $LiBF_4$, $LiPF_6$, lithium triflate, $NaBF_4$, $NaPF_6$, and sodium triflate.

A polymer consist of a large number of repeating units bonded together. A polymerizable unit, in some instances, can be a monomer, oligomer, or low molecular weight polymer that is capable of being polymerized upon activation.

In some embodiments, the N-substituted phenothiazine compounds have stable first and second oxidation states (e.g., radical cation, dication). For example, suitable N-substituted phenothiazine compounds having stable first and second oxidation states include, but are not limited to, two-electron donor compounds having the structure:

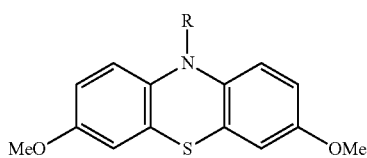

wherein R is selected from alkyl, aryl, alkylaryl, alkoxyaryl, alkylcarboxyl, arylcarbonyl, haloalkyl, perfluoroalkyl, glycol, polyether, haloaryl, a negative electrolyte, a polymerizable unit, and a polymer.

In one embodiment, the two-electron donor compounds include one or more of the structures set forth below:

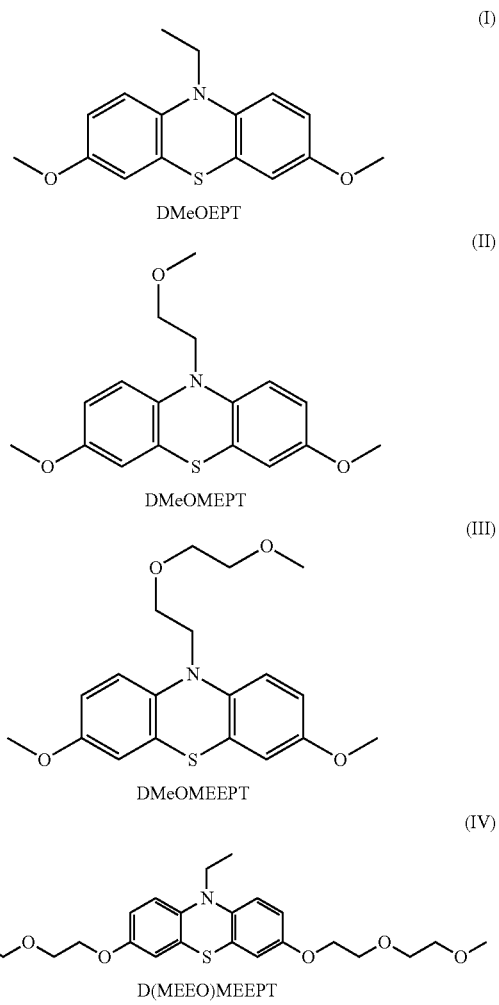

In contrast to most phenothiazines, which decompose in the second oxidation state, the introduction of electron-donating functional groups to the phenothiazine redox-active core facilitates a reversible second oxidation event and/or formation of a doubly oxidized species that is stable for extended periods of time. Accordingly, in some embodiments, the N-substituted phenothiazine compounds described herein provide stable two-electron redox-active materials. For example, as illustrated in FIG. 1 and Table 1, the dimethoxy-substituted phenothiazine derivatives, such as compounds I-IV shown above, provide stable first and second oxidations occurring at about 3.4 and 3.9 V vs. Li, respectively.

TABLE 1

Measured half-wave first and second oxidation potentials and diffusion coefficients.

| Compound | $1^{st}$ $E_{ox}$ vs. Li (V)[a] | $2^{nd}$ $E_{ox}$ vs. Li (V)[a] | Diffusion Coefficient |
|---|---|---|---|
| I | 3.38 | 3.94 | 0.8/0.8 |
| II | 3.42 | 3.96 | 1.0/0.9 |
| III | 3.41 | 3.98 | 0.5/0.5 |
| IV | | | |

[a]Cyclic voltammetry was performed with 10 mM analyte in 0.5M $LiPF_6$ in PC at a scan rate of 100 mV/s.

With regard to Compound IV, oxidation potentials are 0.035 V and 0.625 V vs. ferrocenium/ferrocene in 0.5M TEATFSI/acetonitrile.

In certain embodiments, the stable first and second oxidations facilitate formation of stable dications in non-aqueous electrolytes without requiring an extensive increase (e.g., doubling) of molecular weight. By forming stable dications without extensive increases in molecular weight, the N-substituted phenothiazine compounds described herein provide increased atom economy (i.e., molecular weight per electron). Such atom utilization can be advantageous for both efficiency of the chemical processes and contribute to a greener chemistry process. In one embodiment, for example, the N-substituted phenothiazine compounds described herein increase atom economy by up to 100% as compared to existing compounds and/or catholytes.

Additionally, in some embodiments, the N-substituted phenothiazine compounds described herein provide increased solubility in electrolyte formulations as compared to existing compounds, such as 2,5-di-tert-butyl-1,4-bis(2-methoxyethoxy)benzene (DBBB). In one embodiment, the glyme substituents provide increased solubility in electrolyte formulations as compared to other derivatives. For example, as compared to the N-ethyl derivative, which exhibited a solubility of about 100 mM, the glyme and diglyme derivatives exhibited higher solubility while retaining stable redox chemistry. In another embodiment, this solubility in organic solvents permits the use of renewable earth-abundant elements.

In some embodiments, the N-substituted phenothiazine compounds described herein provide a multi-electron donor including high stability and solubility in catholyte formulations. In another embodiment, the catholyte material provides a multi-electron donor that retains high chemical stability when charged. In a further embodiment, as catholyte energy density is limited due to solubility, stability, and redox chemistry, the high solubility, ability to act as a multi-electron donor, and/or high chemical stability of the compounds described herein significantly increases volumetric energy density as compared to other catholyte materials. For example, when formulated at its solubility limit, diglyme-dimethoxyphenothiazine may provide approximately 5 times the volumetric energy of DBBB, which has an energy density of 10 Ah/L when formulated as a catholyte, and is limited by its solubility (0.4M) and redox chemistry, acting as a single electron donor.

Figure 2:
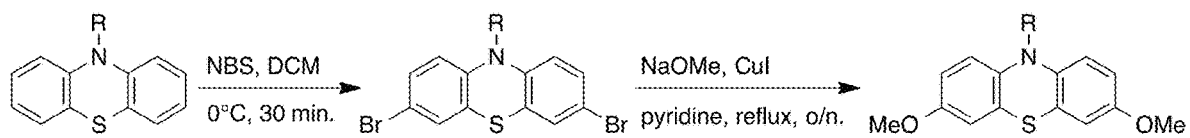
FIG. 2 is a schematic showing synthesis of N-substituted 3,7-dimethoxyphenothiazine derivatives.

The presently-disclosed subject matter also includes a method of making an N-substituted phenothiazine derivative. As illustrated in FIG. 2, in some embodiments, the method includes synthesizing an N-substituted phenothiazine according to previously reported procedures (e.g., Odom, 2014 and Kaur, 2015), forming a 3,7-dibromophenothiazine derivative through aromatic dibromination, and then forming a 3,7-dimethoxyphenothiazine derivative through methoxylation of the dibromophenothiazine. In one embodiment, the methoxylation includes treatment with sodium methoxide and copper (I) iodide in refluxing pyridine. Non-limiting examples of process conditions are provided below in Examples 1-3. In some embodiments, the reactions are scalable.

The presently-disclosed subject matter also includes a non-aqueous redox flow battery. In some embodiments, the non-aqueous redox flow battery includes a negative electrode immersed in a first non-aqueous liquid electrolyte solution, a positive electrode immersed in a second non-aqueous liquid electrolyte solution, and a semi-permeable separator interposed between the negative and positive electrodes. In one embodiment, the second non-aqueous liquid electrolyte solution includes one or more of the N-substituted phenothiazine compounds described herein. For example, in another embodiment, the one or more N-substituted phenothiazine compounds form the electro-active material for the catholyte of the non-aqueous redox flow batteries. In other embodiments, the presently disclosed invention includes a positive cell comprising a cathode and a catholyte including one or more of the N-substituted phenothiazine compounds described herein.

In certain embodiments, the one or more N-substituted phenothiazine compounds include two electron-donating groups per phenothiazine, which approximately doubles electrode capacity, increases atom economy in redox flow batteries, and/or decreases battery cost as compared to phenothiazine compounds having one electron-donating group.

The presently disclosed subject matter is also directed to making a non-aqueous redox flow battery. The method of making a non-aqueous redox flow battery includes immersing a negative electrode in a first non-aqueous liquid electrolyte solution, immersing a positive electrode in a second non-aqueous liquid electrolyte solution, and interposing a semi-permeable separator between the negative and positive electrodes. The second non-aqueous liquid electrolyte solution including one or more of the N-substituted phenothiazine compounds described herein.

The non-aqueous liquid electrolyte solution of the presently-disclosed non-aqueous redox flow battery comprises an organic solvent, which can be selected, for example, from a carbonate solvent, a nitrile, an ether, an aromatic compound, and an ester. Examples of appropriate carbonate solvents include, but are not limited to propylene carbonate, ethylene carbonate, ethyl methylcarbonate, diethylcarbonate, and dimethylcarbonate. Examples of appropriate nitriles include, but are not limited to acetonitrile, 1,4-dicyanobutane, 1,6-dicyanohexane. Examples of appropriate ethers include, but are not limited to diethylether, ether, 1,4-dioxane, diethylene glycol diethyl ether, ethyl ether, and tetrahydrofuran. Examples of aromatic compounds include, but are not limited to, benzene, toluene, pentene, xylenes, chlorobenzene, anisole, and 1,2-dichlorobenzene. An example of a glycol includes, but is not limited to, triethylene glycol. Examples of esters include, but are not limited to, ethyl acetate. Other solvents are described, for example, in R. M. Darling et al., Pathways to low cost electrochemical energy storage: a comparison of aqueous and nonaqueous flow batteries, Energy Environ, Sci., 2014, 7, 3459-3477, incorporated by reference in its entirety.

In some embodiments, the solvent is a polar solvent. Polar organic solvents include, but are not limited to, acetonitrile, acetone, tetrahydrofuran, acetic acid, acetyl acetone, 2-aminoethanol, aniline, anisole, benzene, benzonitrile, benzyl alcohol, 1-butanol, 2-butanol, i-butanol, 2-butanone, t-butyl alcohol, carbon disulfide, carbon tetrachloride, chlorobenzene, chloroform, cyclohexanol, cyclohexanone, di-n-butylphthalate, 1,1-dichloroethane, dichloroethane, diethylamine, diethylene glycol, diglyme, dimethoxyethane (glyme), N,N-dimethylaniline, N,N-dimethylformamide (DMF), dimethylphthalate, dimethylsulfoxide (DMSO), dioxane, ethanol, ethyl acetate, ethyl acetoacetate, ethyl benzoate, ethylene glycol, heptane, hexane, methanol, methyl acetate, methyl t-butyl ether (MTBE), methylene chloride, 1-octanol, 1-pentanol, 2-pentanol, 3-pentanol, 2-pentanone, 3-pentanone, 1-propanol, 2-propanol, pyridine, and tetrahydrofuran(THF).

In other embodiments, the non-aqueous liquid is an ionic liquid. When an ionic liquid is used in a non-aqueous system, this is preferably an inorganic salt made of the combination of cations including, but not limited thereto, ammonium, immidazolium, piperidinium, pyrrolidinium, phophosium and sulfonium cations with anions including, but not limited thereto, diethyl phosphate, bromide, iodide, chloride, methylsulfate, dodecylbenzenesulfonate, trimethylpentyl)phosphinate, dicyanamide, decanoate, triflate, bis (trifluoromethylsulfonyl)imide, 1,1,2,2-tetrafluoroethanesulfonate, perfluorobutanesulfonate, hexafluorophosphates, tetrafluoroborates, sulphate, sulfonate, phosphate, thiocyanate, dicyanamide, acetate, trifluoroacetate, nitrate, tetrachloroferrate, tetrathiocyanocobaltate and methylcarbonate.

The non-aqueous redox flow batteries of the presently disclosed invention include a semi-permeable separator. Non-limiting examples of suitable separator materials include sulfonated tetrafluoroethylene-based fluoropolymer-copolymers, such as NAFION® type ion exchange membranes, sulfonated poly(ether ether ketones), polysulfones, polyethylene, polypropylene, ethylene-propylene copolymers, polyimides, polyvinyldifluorides, and the like, which can be in the form of membranes, matrix-supported gels, sheets, films, or panels. Other suitable materials include porous ceramics, porous insulated metals, cation-conducting glasses, and zeolites. Other porous films, panels or mesh will be readily understood by those skilled in the art.

The compounds used in the non-aqueous redox flow battery has high solubility. In some embodiments, the compound has a solubility of about 0.5M or greater. In some embodiments, the compound has a solubility of about 1.0M or greater. In some embodiments, the compound has a solubility of about 2.0M or greater. In some embodiments, the compound has a solubility of about 3.0M or greater. In some embodiments, the compound has a solubility of about 4.0M or greater. In some embodiments, the compound has a solubility of about 5.0M or greater. In some embodiments, the compound has a solubility in the non-aqueous liquid electrolyte solution of about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0M. The high solubility of the compounds disclosed herein in conjunction with the non-aqueous redox flow battery provides a higher capacity battery that can be used in commercial applications.

In some embodiments, the electro-active compound is part of a polymer. In this regard, the relative concentration of electro-active moiety can be described, rather than that of the entire polymer chain. For example, if a repeat unit of 1,000 monomers was included, then the concentration of monomer can be described, instead of the concentration the polymer chain, because in that case, the concentration of polymer would be about 1000× lower than the concentration of electro-active moiety.

In some embodiments, the non-aqueous electrolyte solution comprises a metal halide salt. Non-limiting examples of the metal halide salt include $LiBF_4$, $NaBF_4$, $LiPF_6$, $NaPF_6$, lithium bis(oxalato)borate, tetra-n-butylammonium hexafluorophosphate tetra-n-butylammonium bromide, tetra-n-butylammonium tetrafluoroborate. In some embodiments, the electrolyte solution can include an ionic liquid dissolved in an organic solvent. The ionic liquid dissolved in the organic solvent can be, for example, an inorganic salt made of the combination of cations including, but not limited thereto, ammonium, immidazolium, piperidinium, pyrrolidinium, phophosium and sulfonium cations with anions including, but not limited thereto, diethyl phosphate, bromide, iodide, chloride, methylsulfate, dodecylbenzenesulfonate, trimethylpentyl)phosphinate, dicyanamide, decanoate, triflate, bis(trifluoromethylsulfonyl)imide, 1,1,2, 2-tetrafluoroethanesulfonate, perfluorobutanesulfonate, hexafluorophosphates, tetrafluoroborates, sulphate, sulfonate, phosphate, thiocyanate, dicyanamide, acetate, trifluoroacetate, nitrate, tetrachloroferrate, tetrathiocyanocobaltate and methylcarbonate.

In some embodiments, the metal halide salt comprises a cation such as, for example, $Li^+$ and $Na^+$. In some embodiments, the metal halide salt comprises anions such as, for example, $BF_4^-$, $PF_6^-$, $ClO_4^-$, $AsF_6^-$, $CF_3SO_3^-$, $N(SO_2CF_3)_2^-$, $N(SO_2CF_2CF_3)_2^-$, $B(C_2O_4)^{2-}$, and $B_{12}X_6H_{(12-n)}^{2-}$, wherein X is a halogen.

The electrodes utilized according to the invention can include metal, a carbon material, or a combination thereof. Examples include platinum, copper, aluminum, nickel or stainless steel, acetylene black, carbon black, activated carbon, amorphous carbon, graphite, graphene, or a nanostructured carbon material, or a combination thereof. The electrode can be porous, fluted, or smooth.

In some instances the redox flow battery includes the redox flow battery shown in U.S. Patent Application Publication No. 2013/0224538 to Jansen et al., which is incorporated herein by this reference.

In some instances, the non-aqueous redox flow battery provides stability over about 500 cycles, 600 cycles, 700 cycles, 800 cycles, 900 cycles or 1000 cycles or more.

While the terms used herein are believed to be well understood by those of ordinary skill in the art, certain definitions are set forth to facilitate explanation of the presently-disclosed subject matter. Unless defined otherwise, all technical and scientific terms used herein have the same meaning as is commonly understood by one of skill in the art to which the invention(s) belong.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

EXAMPLES

Materials and Methods for Examples 1-3.

Hexanes, diethyl ether, and ethyl acetate were Macron brand purchased from VWR. Copper (I) iodide (98%) was purchased from Acros Organics. Magnesium sulfate was purchased from Fisher Scientific. Anhydrous methanol (99.8%), anhydrous pyridine (99.8%), and sodium were purchased from Sigma-Aldrich. Silica gel (65×250 mesh) was purchased from Sorbent Technologies. $^1$H and $^{13}$C NMR spectra were obtained on Varian spectrometers in DMSO-$d_6$ from Cambridge Isotope Laboratories. Propylene carbonate and LiPF$_6$ were battery grade and purchased from BASF Corporation (Florham Park, N.J.).

Dimethoxy-Substitutedphenothiazine Derivative Synthesis:

Dimethoxy-substituted phenothiazine derivatives were prepared in two steps from previously synthesized N-substituted phenothaizines (FIG. 2). In the first step, aromatic dibromination lead selectively to the 3,7-dibromophenothiazine derivatives. Methoxylation of the dibromophenothaizines was afforded by treatment with sodium methoxide and copper (I) iodide in refluxing pyridine. This reaction afforded the desired products in 45-91% yield. DMeOEPT (R=CH$_2$CH$_3$) and DMeOMEPT (R=CH$_2$CH$_2$OCH$_3$) were isolated as white crystalline solids, while DMeOMEEPT (R=(CH$_2$CH$_2$O)$_2$CH$_3$) was isolated as a colorless oil. The products were characterized by 1H and 13C NMR, mass spectrometry, melting point (if crystalline), elemental analysis and single crystal x-ray diffraction (if crystalline) to confirm identity and purity.

Figure 3:
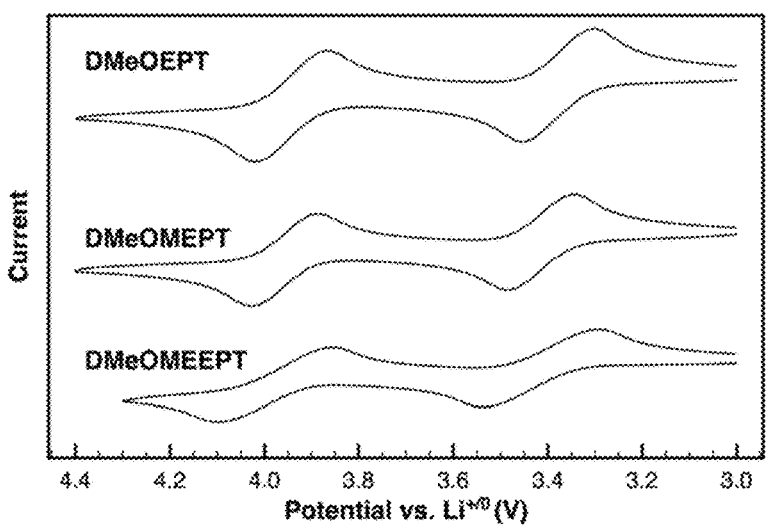
FIG. 3 is a graph showing cyclic voltammograms of DMeOEPT, DMeOMEPT, and DMeOMEEPT in $PC/LiBF_4$.

Electrochemical Analysis:

The cyclic voltammetry experiments illustrated in FIG. 3 were performed with a CH Instruments 650E potentiostat using a three-electrode system with glassy carbon as the working electrode, Li metal as the reference electrode, and a Pt wire as a counter electrode. Each solution contained 10 mM analyte and 0.5M LiBF$_4$ in PC. Voltammograms were recorded at a scan rate of 100 mV/s. Oxidation potentials are reported relative to Li$^{+/0}$.

Figure 4:
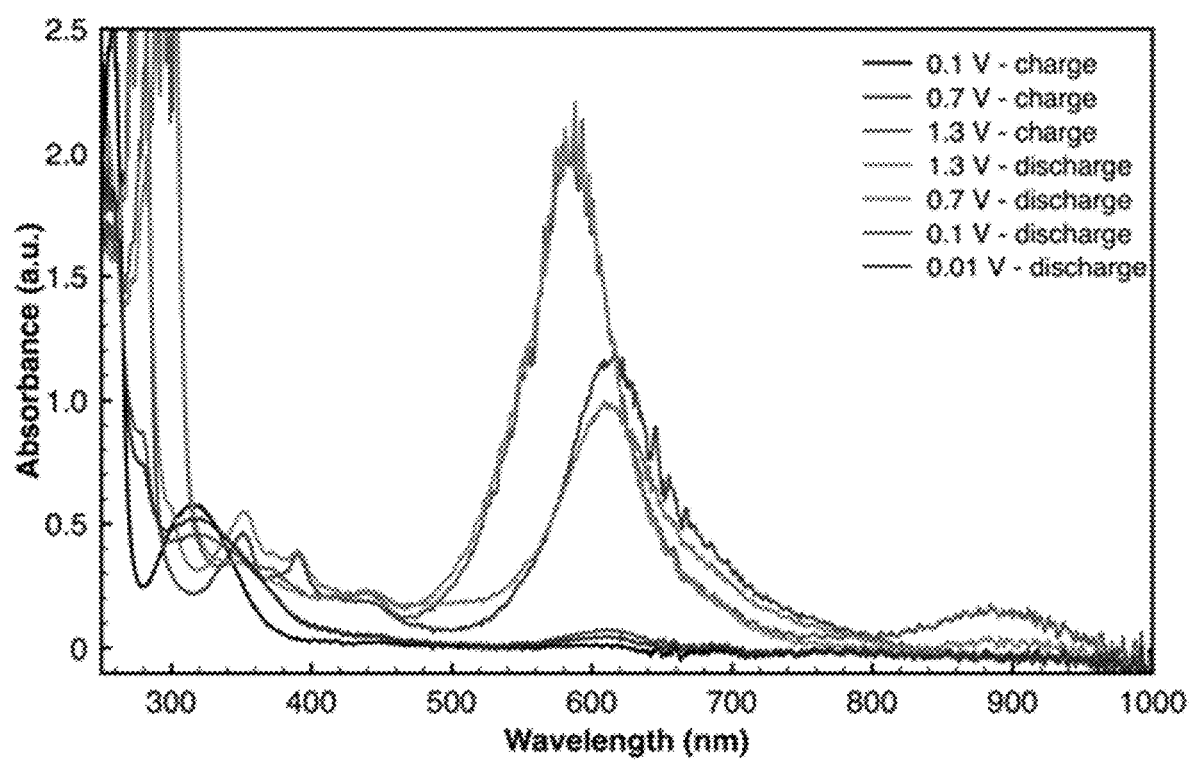
FIG. 4 is a graph showing UV-vis spectra monitored at various potentials for a solution of DMeOEPT at 0.375 mM in a spectroelectrochemical cell containing Pt honeycomb electrode card and a freshly anodized Ag/AgCl electrode in 0.1M LiTFSI in PC.

Spectroelectrochemistry:

The results of spectroelectrochemical measurements on 0.375 mM DMeOEPT in 0.1M LiTFSI in PC are illustrated in FIG. 4. These data show that two distinct species are formed at each oxidation event, further supporting the formation of a radical cation, then a dication, in two separate events, rather than one two-electron-transfer event. Spectroelectrochemical measurements were performed using the spectroelectrochemical cell kit obtained from Pine research. 1 mL of the sample solution was placed in the quartz cuvette equipped with a Pt honeycomb electrode card, used as the working and the counter electrode and a freshly anodized Ag/AgCl electrode, used as the reference electrode. UV-vis spectra were obtained on an Agilent 8453 diode array spectrometer and electrochemical analysis was performed using a CH Instruments 650E potentiostat. First a UV-vis spectrum and a cyclic voltammogram was recorded on the sample. Bulk electrolysis (with coulometery) was then performed for 1 min at 0.1 V increments from 0 to 1.5 V and then back to 0 V; followed by a UV-vis measurement at each of those potentials. The chosen potential window was obtained from cyclic voltammogram measurement.

Example 1: Preparation of 3,7-dimethoxy-N-ethyl-phenothiazine

N-Ethyl-phenothiazine and 3,7-dibromo-N-ethyl-phenothiazine were prepared by previously reported procedures. Odom, 2014 and Kaur, 2015.

3,7-dimethoxy-N-ethyl-phenothiazine

Sodium methoxide (~5M in methanol) solution was prepared by dissolving 0.25 g sodium (9.6 mmol) in 2.0 mL methanol in a round bottom flask at 0° C. under a N$_2$ atmosphere. To the resultant methoxide solution, CuI (763 mg, 4.01 mmol), 3,7-dibromo-N-ethyl-phenothiazine (383 g, 1.00 mmol), and pyridine (5 mL) were added. The reaction mixture was sparged with dry nitrogen for 15 minutes. A reflux condenser was attached and the reaction was heated at 120° C. for 12 hours. Upon completion of the reaction, the reaction mixture was diluted with diethyl ether and washed with brine. The organic extracts were dried over magnesium sulfate, filtered and concentrated under reduced pressure. The organic residue was purified by silica gel chromatography using 0-10% ethyl acetate in hexane as eluent to afford the product as a white crystalline solid (264 mg) in 91% yield. The product was further recrystallized from aqueous methanol solution. $^1$H NMR (DMSO-$d_6$, 400 MHz, ppm) δ 6.88-6.90 (m, 2H), 6.75-6.77 (m, 4H), 3.79 (q, J=6.8 Hz, 2H), 3.33 (s, 6H), 1.24 (t, J=6.8 Hz, 3H), $^{13}$C NMR (DMSO-$d_6$, 100 MHz, ppm) δ 154.5, 138.4, 124.3, 115.9, 112.9, 112.4, 55.4, 41.1, 12.8. GCMS: m/z 287 (41%), 258 (100%), 215 (18%). Anal. calcd. for C$_{16}$H$_{17}$NOS C, 66.87; H, 5.96; N, 4.87. Found C, 66.70; H, 5.94; N, 4.95. Melting point: 115-116° C. (aq. MeOH).

Example 2: Preparation of 3,7-dimethoxy-N-methoxyethyl-phenothiazine 3,7-dibromo-N-methoxyethyl-phenothiazine N-methoxyethyl-phenothiazine (0.251 g, 0.973 mmol) was dissolved in DMF (3 mL). The reaction mixture was cooled in an ice bath and N-bromosuccinimide (0.397 g, 2.23 mmol) was added portion-wise over 10 minutes. The reaction was allowed to warm to room temperature and stirred overnight. Upon completion of the reaction, the reaction mixture was diluted with ethyl acetate and washed with water, sodium thiosulfate solution and brine. The organic extracts were dried over magnesium sulfate, filtered and concentrated under reduced pressure. The organic residue was purified by silica gel chromatography using 0-10% ethyl acetate in hexane as eluent to afford the product as a white crystalline solid (332 mg) in 82% yield. The product was further recrystallized from ethanol solution. $^1$H NMR (DMSO-$d_6$, 400 MHz, ppm) δ 7.36 (m, 4H), 6.99 (m, 2H), 4.01 (t, J=5.6 Hz, 2H), 3.61 (t, J=5.6 Hz, 2H), 3.24 (s, 3H). $^{13}$C NMR (DMSO-d$_6$, 100 MHz, ppm) δ 143.6, 130.3, 129.0, 125.2, 117.5, 114.2, 68.6, 58.2, 47.0. GCMS: m/z 413/415/417 (61%), 368/370/372 (100%), 354/356/358 (22%), 336/338/340 (24%), 289/291 (42%), 196 (26%). Anal. calcd. for C$_{15}$H$_{13}$NOSBr$_2$ C, 43.40; H, 3.16; N, 3.37. Found C, 43.45; H, 2.98; N, 3.25. Melting point: 88-89° C. (EtOH).

3,7-dimethoxy-N-methoxyethyl-phenothiazine

A concentrated sodium methoxide solution was prepared by dissolving 0.13 g sodium (5.7 mmol) in 2 mL methanol. To the methoxide solution, CuI (461 mg, 2.42 mmol), 3,7-dibromo-N-methoxyethyl-phenothiazine (0.249 g, 0.599 mmol) and pyridine (3 mL) were added. The reaction mixture was sparged with nitrogen for 15 minutes. A reflux condenser was attached and the reaction was heated at 120° C. for 12 hours. Upon completion of the reaction, the reaction mixture was diluted with diethyl ether and washed with brine. The organic extracts were dried over magnesium sulfate, filtered and concentrated under reduced pressure. The organic residue was purified by silica gel chromatography using 0-10% ethyl acetate in hexane as eluent to afford the product as a white crystalline solid (132 mg) in 69% yield. The product was further recrystallized from ethanol solution. $^1$H NMR (DMSO-d$_6$, 400 MHz, ppm) δ 6.92 (m, 2H), 6.75 (m, 4H), 3.93 (t, J=5.6 Hz, 2H), 3.69 (s, 6H), 3.59 (t, J=5.6 Hz, 2H), 3.24 (s, 3H). $^{13}$C NMR (DMSO-d$_6$, 100 MHz, ppm) δ 154.7, 138.5, 124.6, 116.1, 112.9, 112.4, 69.0, 58.2, 55.4, 47.0. GCMS: m/z 317 (100%), 272 (100%), 258 (86%), 240 (73%), 215 (22%), 172 (13%). Anal. calcd. for C$_{17}$H$_{19}$NO$_3$S C, 64.33; H, 6.03; N, 4.41. Found C, 64.46; H, 6.01; N, 4.45. Melting point: 108-110° C. (EtOH).

Example 3: Preparation of 3,7-dimethoxy-N-((2-methoxy)ethoxy)ethyl-phenothiazine 3,7-dibromo-N-((2-methoxy)ethoxy)ethylphenothiazine N-((2-methoxy)ethoxy)ethylphenothiazine (1.12 g, 3.73 mmol) was dissolved in anhydrous dichloromethane (DCM) (11 mL) in a round-bottomed flask. The reaction mixture was cooled in an ice bath and N-bromosuccinimide (2.0 g, 11.2 mmol) was added portion-wise over 10 minutes. The reaction was allowed to stir at 0° C. for 30 min. Upon completion of the reaction, the reaction mixture was quenched with sodium thiosulfate, diluted with DCM, and then the organic layer washed with water and brine. The organic extracts were dried over magnesium sulfate, filtered and concentrated under reduced pressure. The organic residue was purified by silica gel chromatography using 40% ethyl acetate in hexane as eluent to afford the product as a pale red syrup (1.03 g) in 60% yield. $^1$H NMR (DMSO-d$_6$, 400 MHz, ppm) δ 7.35 (m, 4H), 7.00 (dd, 2H, J=6.8, 2.8), 4.00 (t, 2H, J=5.6), 3.69 (t, 2H, J=5.6), 3.51 (m, 2H), 3.40 (m, 2H), 3.19 (s, 3H). $^{13}$C NMR (DMSO-d$_6$, 100 MHz, ppm) δ 144.1, 130.8, 129.5, 125.7, 118.1, 114.6, 71.7, 70.1, 67.6, 58.5, 47.8. GCMS: m/z 457/459/461 (63%), 368/370/372 (100%), 354/356/358 (25%), 336/338/340 (16%), 289/291 (31%), 207 (18%), 196 (26%). Anal. calcd. for C$_{17}$H$_{17}$NO$_2$SBr$_2$ C, 44.47; H, 3.73; N, 3.05. Found C, 44.61; H, 3.74; N, 3.05.

3,7-dimethoxy-N-((2-methoxy)ethoxy)ethyl-phenothiazine

Sodium methoxide (~3M in methanol) solution was prepared by dissolving 0.50 g sodium (22 mmol) in 7 mL methanol. To the methoxide solution, CuI (1.65 g, 8.68 mmol), DiBrMEEPT (1.00 g, 2.17 mmol) and pyridine (10.8 mL) were added. The reaction mixture was purged with nitrogen for 15 minutes. A reflux condenser was attached and the reaction was heated at 120° C. for 12 hours. Upon completion of the reaction, the reaction mixture was diluted with diethyl ether and washed with brine. The organic extracts were dried over magnesium sulfate, filtered and concentrated under reduced pressure. The organic residue was purified by silica gel chromatography using 40% ethyl acetate in hexane as eluent to afford the product as a colorless syrup (350 mg) in 45% yield. $^1$H NMR (DMSO-d$_6$, 400 MHz, ppm) δ 6.93 (dt, 2H, J=9.2, 1.4), 6.76 (m, 4H), 3.93 (t, 2H, J=5.6), 3.69 (s, 6H), 3.68 (t, 2H, J=5.6), 3.52 (m, 2H), 3.41 (m, 2H), 3.21 (s, 3H). $^{13}$C NMR (DMSO-d$_6$, 100 MHz, ppm) δ 154.7, 138.5, 124.6, 116.1, 112.9, 112.4, 71.2, 69.6, 67.5, 58.0, 55.4, 47.3. GCMS: m/z 361 (77%), 272 (100%), 258 (78%), 240 (60%), 215 (26%), 172 (12%). Anal. calcd. for C$_{19}$H$_{23}$NO$_4$S C, 63.14; H, 6.41; N, 3.88. Found C, 63.16; H, 6.55; N, 3.90.

Example 4: Preparation of D(MEEO)MEEPT

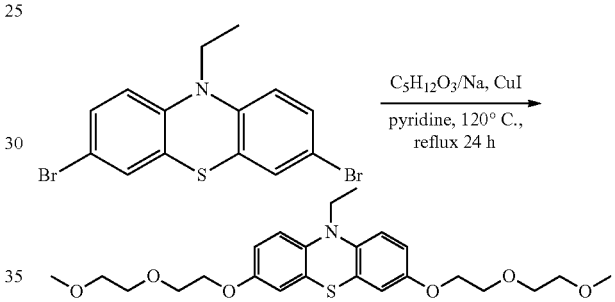

An oven-dried 1 L round-bottomed flask was transferred to an argon filled glove box, then diethylene glycol monomethyl ether (390 mL, 3.41 mol) was added into the round-bottomed flask and removed it from the glove box. Freshly cut sodium metal (9.562 g, 415.5 mmol) was dissolved in diethylene glycol monomethyl ether under nitrogen atmosphere. Then, copper (i) iodide (31.65 g, 168.2 mmol), 3,7-dibromo-N-ethylphenothiazine (16.00 g, 41.55 mmol) and anhydrous pyridine (320 mL) were added to the resultant solution. After that reaction mixture was sparged with nitrogen about 15 min while stirring. The round-bottomed flask was immersed in an oil bath and heated to 120° C. for overnight after connecting a reflux condenser. Upon completion of the reaction, reaction mixture was concentrated by using rotovap. Then reaction mixture was diluted with ethyl acetate and washed with 1M aq. HCl, water and brine. The combined organic extracts were dried over magnesium sulphate and concentrated by using rotary evaporation. Finally, organic residue was purified on a silica gel column using 20-50% ethyl acetate in hexanes. The silica gel was neutralized with trimethylamine (2-3 mL) during packing the column. The product was yellow/light red viscous liquid (14.8 g, 77%). A saturated solution of D(MEEO)EPT-BF$_4$ salt in DCM was prepared. A small volume was transferred in a NMR tube and carefully layered it with toluene to form two distinct layers. Finally, the NMR tube was capped and placed in a freezer, and crystals formed at the interface of the solvents. $^1$H NMR (DMSO-d$_6$, 400 MHz, ppm)) δ 6.90-6.85 (m, 2H), 6.79-6.75 (m, 4H), 4.05-3.98 (m, 4H), 3.79 (q, J=6.9 Hz, 2H), 3.71-3.65 (m, 4H), 3.58-3.52 (m, 4H), 3.47-3.41 (m, 4H), 3.23 (s, 6H), 1.23 (t, J=6.9 Hz, 3H). $^{13}$C NMR ((DMSO-d$_6$, 100 MHz, ppm) δ 153.91, 138.66, 124.47, 116.02, 113.79, 113.31, 71.47, 69.88, 69.14, 67.81, 58.26, 41.33, 12.93. GCMS: m/z 463 (100%), 434 (30%), 360 (11%), 230 (14%), 103(18%), 59(47%). Anal. calcd. for C$_{24}$H$_{33}$NO$_6$S C, 62.18; H, 7.18; N, 3.02; O, 20.71; S, 6.92. Found C, 62.40; H, 7.22; N, 3.03.

Figure 5:
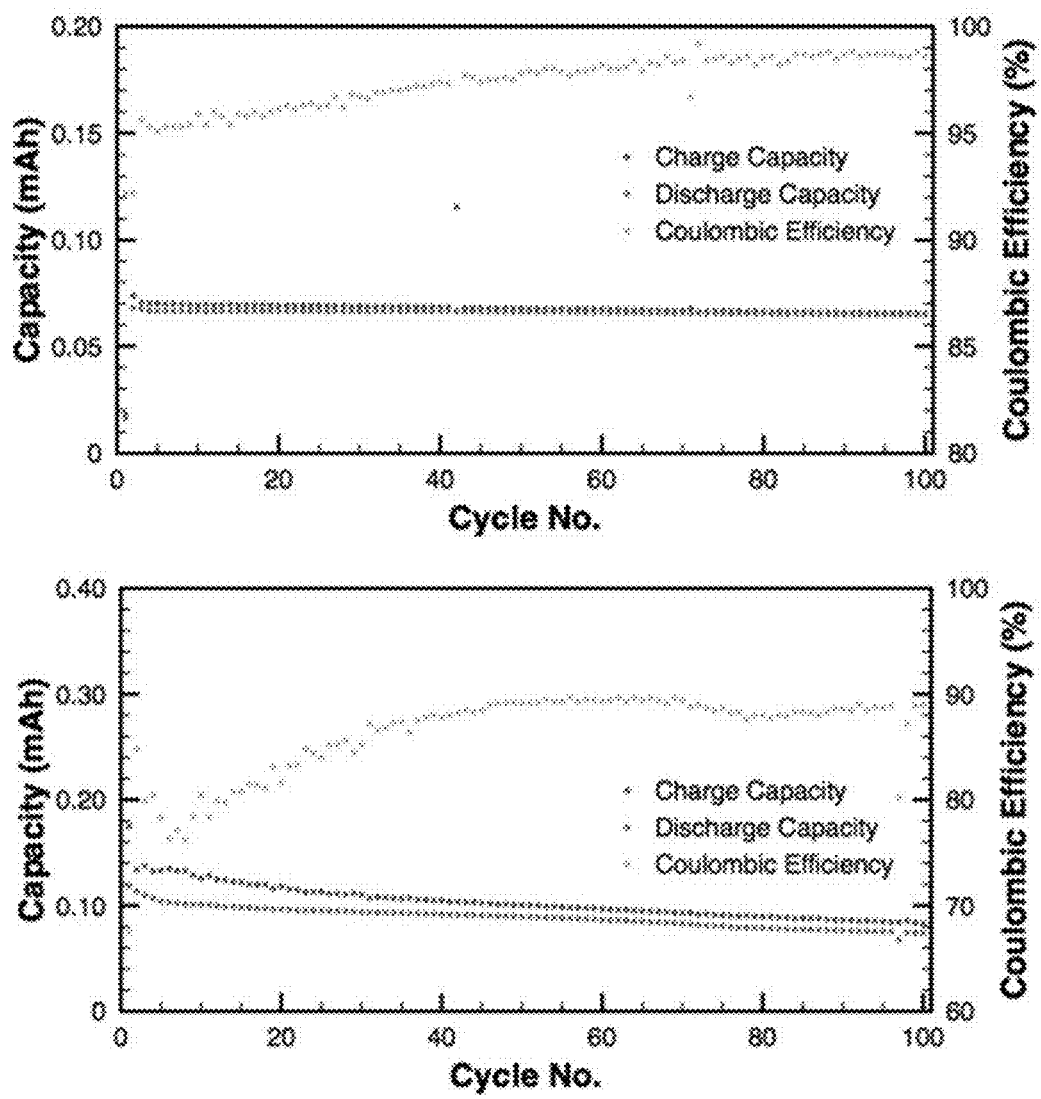
FIG. 5 shows graphs illustrating DMeOEPT half-cell cycling accessing only the first oxidation state (left) and both first and second oxidations (right).
Figure 6:
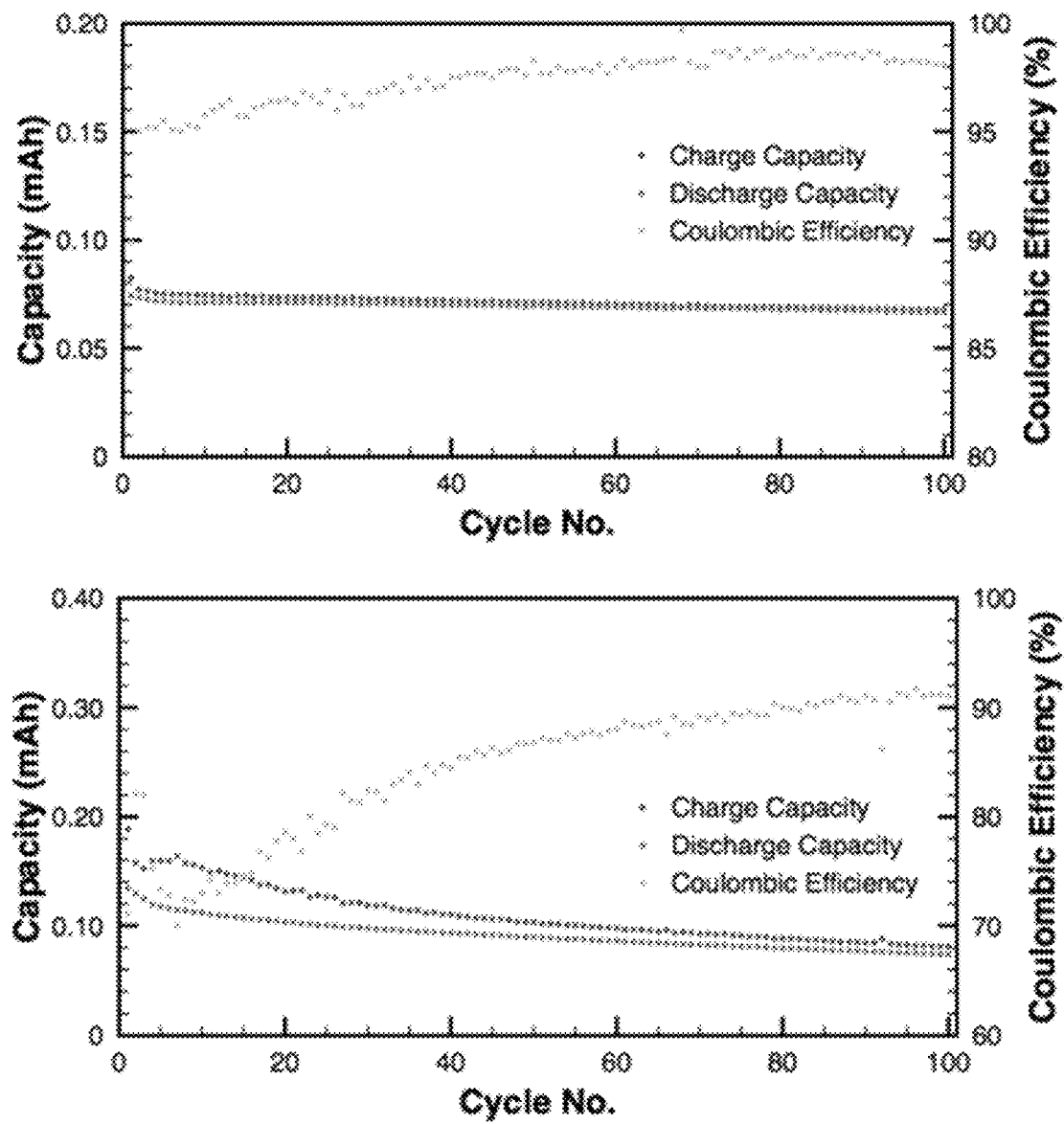
FIG. 6 shows graphs illustrating DMeOMEPT half-cell cycling accessing only the first oxidation state (left) and both first and second oxidations (right).
Figure 7:
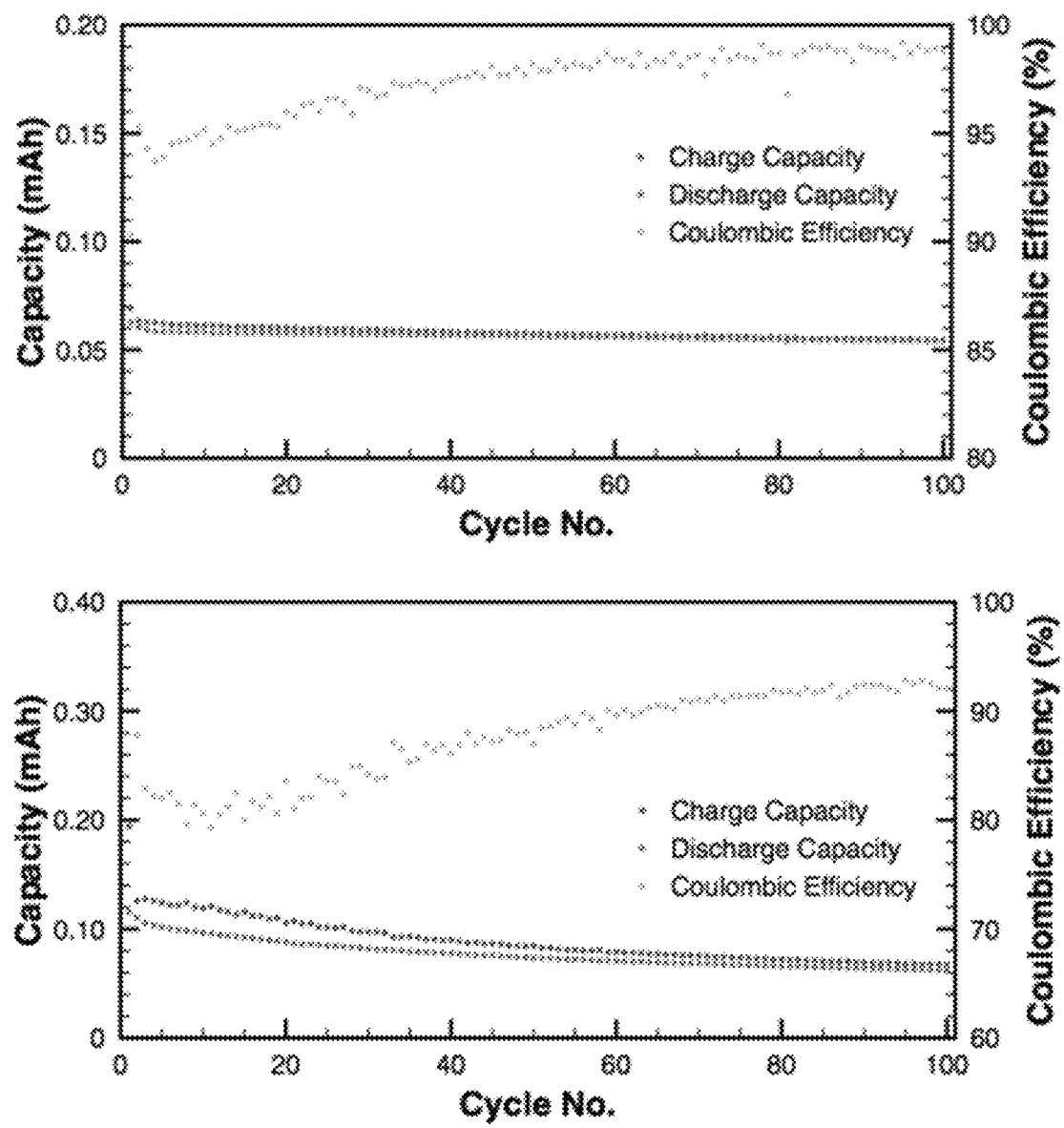
FIG. 7 shows graphs illustrating DMeOMEEPT half-cell cycling accessing only the first oxidation state (left) and both first and second oxidations (right).

Discussion of Examples:

Preliminary experiments to determine the stability of dialkoxyphenothiazines on longer timescales were accomplished by half-cell cycling experiments versus lithium metal. Active material was dissolved at 0.01M in 0.5M LiBF$_4$/PC and soaked into a graphite felt electrode. A 2032 coin cell was assembled with the graphite felt, a lithiated Nafion membrane and lithium metal. For one-electron transfer reactions, the coin cell was cycled between 3.1 and 3.6 V. All three dialkyoxybenzene shows high stability in one-electron cycling with high coulombic efficiency (>95% over 100 cycles) and little loss of active material over 100 cycles (FIGS. 5-7). Such performance suggests that the first oxidation state of these compounds is highly stable and does not react or decompose leading to decreased capacities. Crossover and premature reaction of the oxidized species at the lithium anode may account for the small loss in coloumbic efficiency.

For two-electron transfer reactions, the coin cell was cycled between 3.1 and 4.2 V in order to access the second oxidation state of the dialkoxyphenothiazines. Roughly twice the capacity of the one-electron experiment is observed but with reduced coulombic efficiency (about 80-90%). The reduced coulombic efficiency is likely due to extended charging times leading to increased membrane crossover and premature reduction of the active material. Little loss of active material is observed which is promising as it again suggests that the material is stable in its second oxidation state form. Additionally, as shown by the cyclic voltammetry experiments discussed above (FIG. 3), both first and second oxidation events were reversible and were observed at about 3.4 V and 4.0 V for all three compounds.

All patents, patent applications, publications, and other published materials mentioned in this specification, unless noted otherwise, are herein incorporated by reference to the same extent as if each individual publication, patent, or patent application was specifically and individually indicated to be incorporated by reference, including the references set forth in the following list:

REFERENCES

1. Wang, W.; Luo, Q.; Li, B.; Wei, X.; Li, L.; Yang, Z. Adv. Funct. Mater. 2013, 23, 970-986.
2. Weber, A. Z.; Mench, M. M.; Meyers, J. P.; Ross, P. N.; Gostick, J. T.; Liu, Q. J. Appl. Electrochem. 2011, 41, 1137-1164.
3. Wei, X.; Xu, W.; Huang, J.; Zhang, L.; Walter, E.; Lawrence, C.; Vijayakumar, M.; Henderson, W. A.; Liu, T.; Cosimbescu, L.; Li, B.; Sprenkle, V.; Wang, W. Angew. Chem. Int. Ed. Engl. 2015, 54, 8684-8687.
4. Huang, J.; Su, L.; Kowalski, J. A.; Barton, J. L.; Ferrandon, M.; Burrell, A. K.; Brushett, F. R.; Zhang, L. J. Mater. Chem. A 2015, 3, 14971-14976.
5. Wei, X.; Cosimbescu, L.; Xu, W.; Hu, J. Z.; Vijayakumar, M.; Feng, J.; Hu, M. Y.; Deng, X.; Xiao, J.; Liu, J.; Sprenkle, V.; Wang, W. Adv. Energy Mater. 2015, 5, 1400678.
6. Huang, J.; Cheng, L.; Assary, R. S.; Wang, P.; Xue, Z.; Burrell, A. K.; Curtiss, L. A.; Zhang, L. Adv. Energy Mater. 2015, 5, n/a-n/a.
7. Wei, X.; Xu, W.; Vijayakumar, M.; Cosimbescu, L.; Liu, T.; Sprenkle, V.; Wang, W. Adv. Mater. 2014, 26, 7649-7653.
8. Casselman, M. D.; Kaur, A. P.; Narayana, K. A.; Elliott, C. F.; Risko, C.; Odom, S. A. Phys. Chem. Chem. Phys. 2015, 17, 6905-6912.
9. Kaur, A. P.; Holubowitch, N. E.; Ergun, S.; Elliott, C. F.; Odom, S. A. Energy Technol. 2015, 3, 476-480.
10. Odom, S. A.;* Ergun, S.; Poudel, P. P.; Parkin, S. R. Energy and Environmental Sciences, 2014, 7, 760-767. DOI: 10.1039/C3EE42305K.
11. Kaur, A. P.; C. F.; Ergun, S.; Odom, S. A.,* Journal of the Electrochemical Society, 2016, 163, A1-A7. DOI: 10.1149/2.0951514jes It will be understood that various details of the presently disclosed subject matter can be changed without departing from the scope of the subject matter disclosed herein. Furthermore, the foregoing description is for the purpose of illustration only, and not for the purpose of limitation.

We claim:

1. A compound selected from the group consisting of:

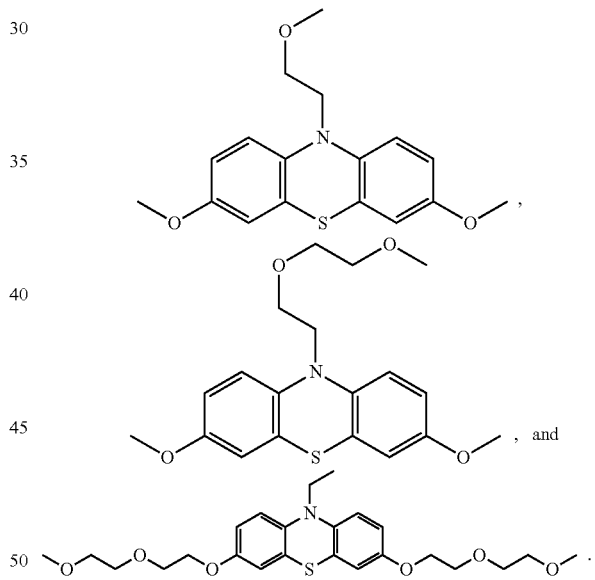

2. The non-aqueous flow-battery, comprising:
a negative electrode immersed in a first non-aqueous liquid electrolyte solution;
a positive electrode immersed in a second non-aqueous liquid electrolyte solution, the second non-aqueous liquid electrolyte solution including at least one compound according to claim 1; and
a semi-permeable separator interposed between the negative and positive electrodes.

* * * * *